(12) United States Patent
Soltz et al.

(10) Patent No.: US 9,254,131 B2
(45) Date of Patent: Feb. 9, 2016

(54) SURGICAL STAPLE WITH AUGMENTED COMPRESSION AREA

(71) Applicant: COVIDIEN LP, Mansfield, MA (US)

(72) Inventors: Michael Soltz, New York, NY (US); Kevin Sniffin, Danbury, CT (US); Jennifer Broom, Branford, CT (US); Henry E. Holsten, Covington, GA (US)

(73) Assignee: Covidien LP, Mansfield, MA (US)

( * ) Notice: Subject to any disclaimer, the term of this patent is extended or adjusted under 35 U.S.C. 154(b) by 181 days.

(21) Appl. No.: 13/706,613

(22) Filed: Dec. 6, 2012

(65) Prior Publication Data

US 2013/0092718 A1    Apr. 18, 2013

Related U.S. Application Data

(62) Division of application No. 12/144,696, filed on Jun. 24, 2008, now Pat. No. 8,348,972.

(60) Provisional application No. 60/959,054, filed on Jul. 11, 2007.

(51) Int. Cl.
*A61B 17/068* (2006.01)
*A61B 17/064* (2006.01)
*A61B 17/072* (2006.01)

(52) U.S. Cl.
CPC ........... *A61B 17/068* (2013.01); *A61B 17/0644* (2013.01); *A61B 17/0643* (2013.01); *A61B 17/072* (2013.01); *A61B 17/07292* (2013.01)

(58) Field of Classification Search
CPC ........................... A61B 17/068; A61B 17/0644

USPC ........................................ 606/219, 139, 142
See application file for complete search history.

(56) References Cited

U.S. PATENT DOCUMENTS

| | | | |
|---|---|---|---|
| 1,376,223 A * | 4/1921 | Pannier | 40/301 |
| 1,756,670 A | 8/1926 | Treat | |
| 3,258,012 A | 6/1966 | Nakayama et al. | |
| 3,744,495 A | 7/1973 | Johnson | |
| 3,771,526 A | 11/1973 | Rudie | |
| 3,837,555 A | 9/1974 | Green | |
| 4,014,492 A | 3/1977 | Rothfuss | |

(Continued)

FOREIGN PATENT DOCUMENTS

| | | |
|---|---|---|
| EP | 0129442 | 12/1984 |
| EP | 0129442 A1 | 12/1984 |

(Continued)

OTHER PUBLICATIONS

European Search Report EP 06016963 dated Mar. 9, 2007; (9 pp.).

(Continued)

*Primary Examiner* — Vy Bui

(57) ABSTRACT

A multi-part surgical staple assembly is provided to provide uniform compression across stapled tissues. The staple assembly generally includes a U-shaped staple, a staple plate positionable against a backspan of the staple for engagement with one side of a stapled tissue section and a platen for receipt of tissue penetrating tips of the staple and engageable with an opposite side of a stapled tissue section. The staple plate and platen are provided with holes to receive the legs of the staple. In one embodiment, the staple plate is provided with a biasing member to bias the staple plate away from the backspan of the staple and toward the stapled tissue.

9 Claims, 5 Drawing Sheets

(56) References Cited

U.S. PATENT DOCUMENTS

| | | | |
|---|---|---|---|
| 4,278,091 A | 7/1981 | Borzone | |
| 4,319,576 A | 3/1982 | Rothfuss | |
| 4,475,679 A | 10/1984 | Fleury, Jr. | |
| 4,531,522 A | 7/1985 | Bedi et al. | |
| 4,532,927 A * | 8/1985 | Miksza, Jr. | 606/220 |
| 4,548,202 A | 10/1985 | Duncan | |
| 4,573,469 A | 3/1986 | Golden et al. | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,627,437 A * | 12/1986 | Bedi et al. | 606/220 |
| 4,741,336 A | 5/1988 | Failla et al. | |
| 4,767,044 A | 8/1988 | Green | |
| 4,809,695 A | 3/1989 | Gwathmey et al. | |
| 4,848,637 A | 7/1989 | Pruitt | |
| 4,881,545 A | 11/1989 | Isaacs et al. | |
| 4,930,503 A | 6/1990 | Pruitt | |
| 4,941,623 A | 7/1990 | Pruitt | |
| 4,978,049 A | 12/1990 | Green | |
| 5,027,834 A | 7/1991 | Pruitt | |
| 5,108,422 A | 4/1992 | Green et al. | |
| 5,180,092 A | 1/1993 | Crainich | |
| 5,201,746 A | 4/1993 | Shichman | |
| 5,209,756 A | 5/1993 | Seedhom et al. | |
| 5,219,353 A | 6/1993 | Garvey, III et al. | |
| 5,240,163 A | 8/1993 | Stein et al. | |
| 5,282,829 A | 2/1994 | Hermes | |
| 5,342,396 A | 8/1994 | Cook | |
| 5,350,400 A | 9/1994 | Esposito et al. | |
| 5,352,229 A | 10/1994 | Goble et al. | |
| 5,425,489 A | 6/1995 | Shichman et al. | |
| 5,439,479 A | 8/1995 | Shichman et al. | |
| 5,441,193 A | 8/1995 | Gravener | |
| 5,452,836 A | 9/1995 | Huitema et al. | |
| 5,452,837 A | 9/1995 | Williamson, IV et al. | |
| 5,470,010 A | 11/1995 | Rothfuss et al. | |
| 5,484,095 A | 1/1996 | Green et al. | |
| 5,497,931 A | 3/1996 | Nakamura | |
| 5,501,693 A | 3/1996 | Gravener | |
| 5,509,920 A | 4/1996 | Phillips et al. | |
| 5,571,116 A | 11/1996 | Bolanos et al. | |
| 5,571,285 A | 11/1996 | Chow et al. | |
| 5,584,856 A | 12/1996 | Jameel et al. | |
| 5,620,452 A | 4/1997 | Yoon | |
| 5,634,926 A | 6/1997 | Jobe | |
| 5,667,526 A | 9/1997 | Levin | |
| 5,667,527 A | 9/1997 | Cook | |
| 5,676,674 A | 10/1997 | Bolanos et al. | |
| 5,697,542 A | 12/1997 | Knodel et al. | |
| 5,709,680 A | 1/1998 | Yates et al. | |
| 5,741,268 A | 4/1998 | Schutz | |
| 5,810,822 A | 9/1998 | Mortier | |
| 5,865,361 A | 2/1999 | Milliman et al. | |
| 5,871,135 A | 2/1999 | Williamson, IV et al. | |
| 5,879,371 A | 3/1999 | Gardiner et al. | |
| 5,915,616 A | 6/1999 | Viola et al. | |
| 5,961,521 A | 10/1999 | Roger | |
| 5,964,394 A | 10/1999 | Robertson | |
| 6,083,242 A | 7/2000 | Cook | |
| 6,202,914 B1 | 3/2001 | Geiste et al. | |
| 6,273,897 B1 | 8/2001 | Dalessandro et al. | |
| 6,325,810 B1 | 12/2001 | Hamilton et al. | |
| 6,348,054 B1 | 2/2002 | Allen | |
| 6,702,826 B2 | 3/2004 | Liddicoat et al. | |
| 6,706,057 B1 | 3/2004 | Bidoia et al. | |
| 6,786,382 B1 | 9/2004 | Hoffman | |
| 6,905,057 B2 | 6/2005 | Swayze et al. | |
| 6,945,444 B2 | 9/2005 | Gresham et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,001,411 B1 | 2/2006 | Dean | |
| 7,044,352 B2 | 5/2006 | Shelton, IV et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,083,075 B2 | 8/2006 | Swayze et al. | |
| 7,111,769 B2 | 9/2006 | Wales et al. | |
| 7,128,254 B2 | 10/2006 | Shelton, IV et al. | |
| 7,140,528 B2 | 11/2006 | Shelton, IV | |
| 7,143,923 B2 | 12/2006 | Shelton, IV et al. | |
| 7,143,925 B2 | 12/2006 | Shelton, IV et al. | |
| 7,147,138 B2 | 12/2006 | Shelton, IV | |
| 7,303,108 B2 | 12/2007 | Shelton, IV | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,398,907 B2 * | 7/2008 | Racenet et al. | 227/176.1 |
| 7,398,908 B2 | 7/2008 | Holsten et al. | |
| 7,404,509 B2 | 7/2008 | Ortiz et al. | |
| 7,434,715 B2 | 10/2008 | Shelton, IV et al. | |
| 7,455,676 B2 | 11/2008 | Holsten et al. | |
| 7,487,899 B2 | 2/2009 | Shelton, IV et al. | |
| 7,500,979 B2 | 3/2009 | Hueil et al. | |
| 7,506,790 B2 | 3/2009 | Shelton, IV | |
| 7,547,312 B2 | 6/2009 | Bauman et al. | |
| 7,641,091 B2 | 1/2010 | Olson et al. | |
| 7,654,431 B2 | 2/2010 | Hueil et al. | |
| 7,794,475 B2 | 9/2010 | Hess et al. | |
| 7,857,183 B2 | 12/2010 | Shelton, IV | |
| 7,887,563 B2 | 2/2011 | Cummins | |
| 8,025,199 B2 | 9/2011 | Whitman et al. | |
| 2004/0073222 A1 | 4/2004 | Koseki | |
| 2004/0093029 A1 | 5/2004 | Zubik et al. | |
| 2004/0247415 A1 | 12/2004 | Mangone, Jr. | |
| 2006/0015144 A1 | 1/2006 | Burbank et al. | |
| 2006/0025810 A1 | 2/2006 | Shelton, IV | |
| 2006/0025812 A1 | 2/2006 | Shelton, IV | |
| 2006/0025813 A1 | 2/2006 | Shelton, IV et al. | |
| 2006/0039779 A1 | 2/2006 | Ringl | |
| 2006/0085030 A1 | 4/2006 | Bettuchi et al. | |
| 2006/0163312 A1 | 7/2006 | Viola et al. | |
| 2006/0291981 A1 | 12/2006 | Viola et al. | |
| 2007/0010838 A1 | 1/2007 | Shelton, IV | |
| 2007/0095877 A1 | 5/2007 | Racenet et al. | |
| 2007/0131732 A1 | 6/2007 | Holsten et al. | |
| 2007/0262116 A1 | 11/2007 | Hueil et al. | |
| 2008/0078800 A1 | 4/2008 | Hess et al. | |
| 2008/0078804 A1 | 4/2008 | Shelton, IV | |

FOREIGN PATENT DOCUMENTS

| | | |
|---|---|---|
| EP | 0169044 | 1/1986 |
| EP | 0169044 A2 | 1/1986 |
| EP | 0588081 | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1607048 | 12/2005 |
| EP | 1785098 | 8/2006 |
| EP | 1728473 | 12/2006 |
| EP | 1754445 | 2/2007 |
| EP | 1875868 | 1/2008 |
| EP | 1917918 | 5/2008 |
| EP | 2095777 | 9/2009 |
| FR | 2838952 | 10/2003 |
| GB | 2029754 | 3/1980 |
| GB | 2051287 | 1/1981 |
| GB | 2019296 | 10/2009 |
| SU | 405234 | 9/1975 |
| SU | 1333319 | 8/1987 |
| SU | 1442191 | 12/1988 |
| SU | 1459659 | 2/1989 |
| WO | WO 86/02254 | 4/1986 |
| WO | WO 90/05489 | 5/1990 |
| WO | WO 96/19146 | 6/1996 |

(56) References Cited

FOREIGN PATENT DOCUMENTS

| WO | WO 97/34533 | 9/1997 |
|---|---|---|
| WO | WO 02/30296 | 4/2002 |
| WO | WO 03/094743 | 11/2003 |
| WO | WO 03/094747 | 11/2003 |
| WO | WO 2006/055385 | 5/2006 |
| WO | WO 2008/007377 | 1/2008 |
| WO | WO 2008/039250 | 4/2008 |
| WO | WO 2008/089050 | 7/2008 |

OTHER PUBLICATIONS

European Search Report EP 09251067 completed Mar. 9, 2011; (6 pp.).
European Search Report EP 09251224 dated Oct. 8, 2009; (3 pp.).
European Search Report EP 09251268 dated Sep. 25, 2009; (6 pp.).
European Search Report EP 09251793 dated Nov. 16, 2009; (9 pp.).
European Search Report EP 10251797 dated Jan. 31, 2011; (7 pp.).
European Search Report for EP 09251240 mailed Oct. 19, 2009; (8 pp.).
European Search Report for EP 08252283 completed Jan. 15, 2009; (13 pp.).
European Search Report EP 11004299 dated Aug. 12, 2011; (6 pp.).
European Search Report EP 07254366 dated Nov. 11, 2010; (7 pp.).
Australian Examiner's Report dated Feb. 20, 2015.
Australian Examiner's Report dated Apr. 8, 2015.
European Search Report corresponding to European Application No. EP 15170322 dated Sep. 30, 2015.

\* cited by examiner

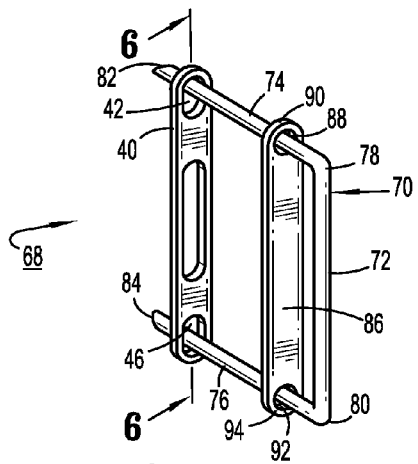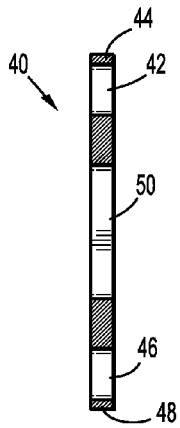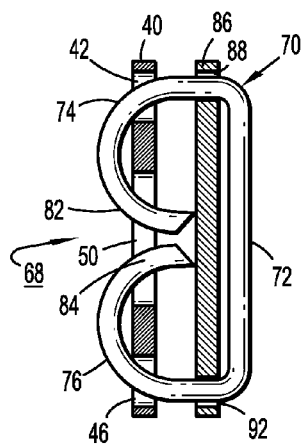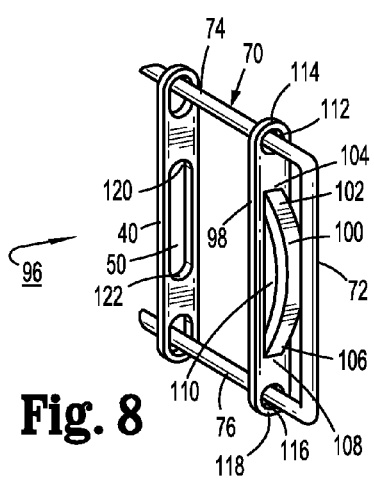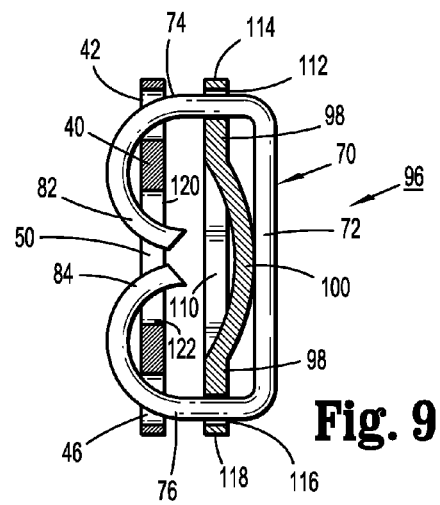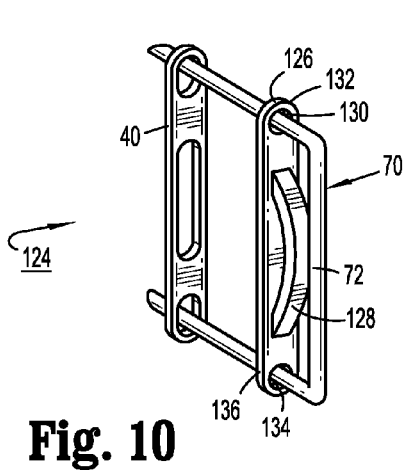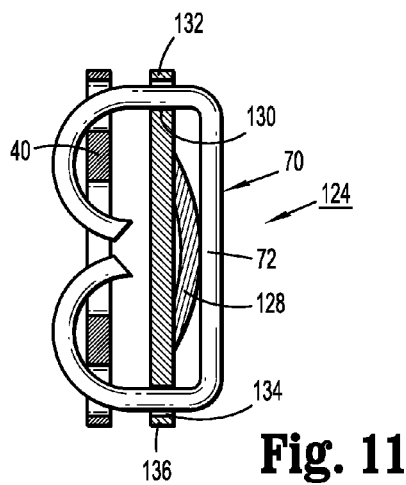

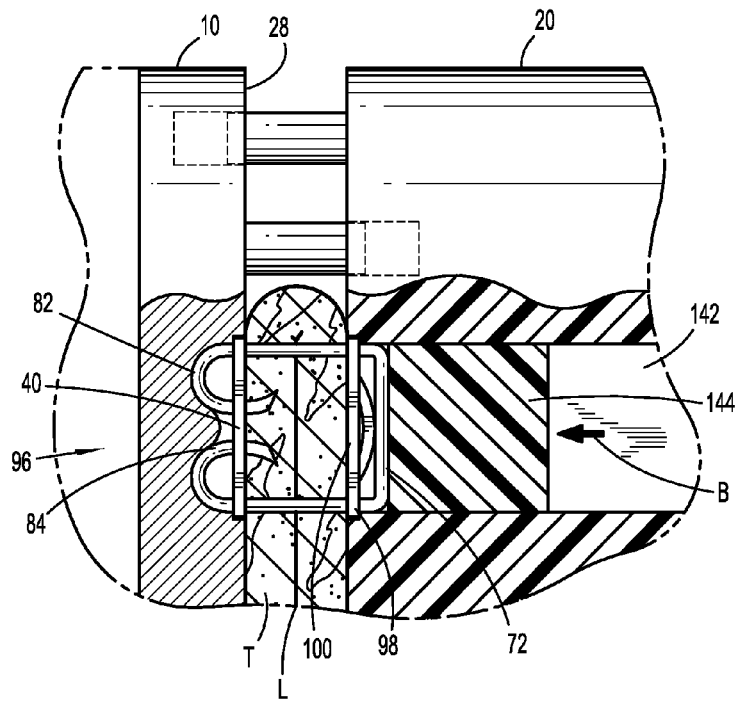
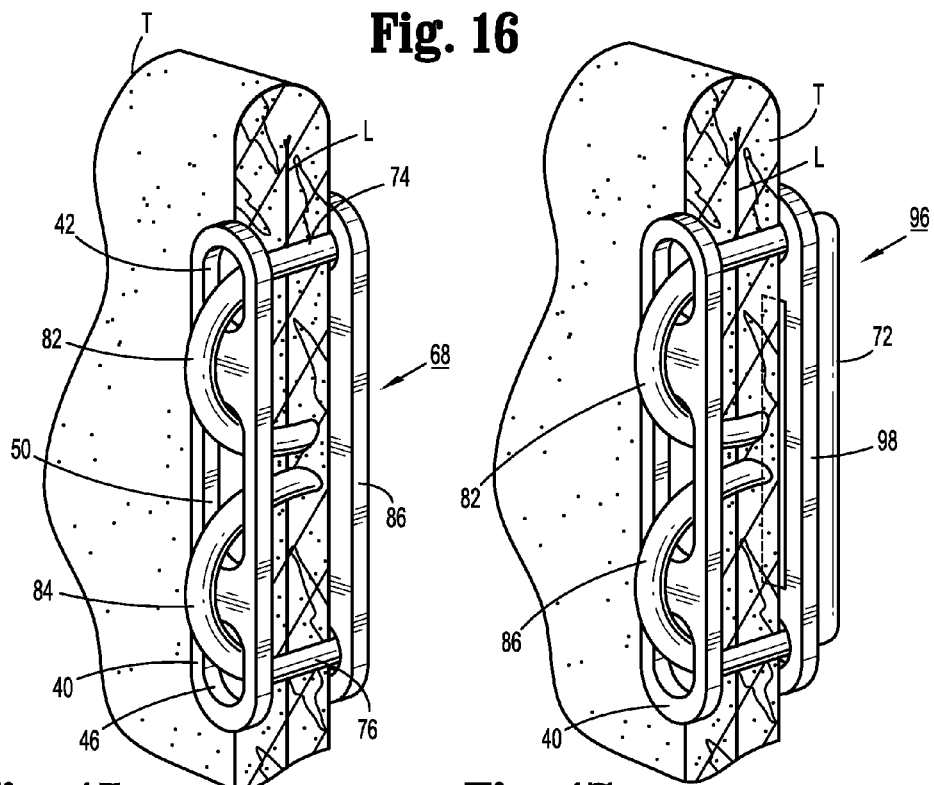
Fig. 16
Fig. 15     Fig. 17

SURGICAL STAPLE WITH AUGMENTED COMPRESSION AREA

CROSS REFERENCE TO RELATED APPLICATIONS

The present application is a divisional application of and claims the benefit of and priority to U.S. patent application Ser. No. 12/144,696, filed on Jun. 24, 2008 by Soltz et al., now U.S. Pat. No. 8,348,972 which claims the benefit of and priority to U.S. Provisional Application No. 60/959,054, filed on Jul. 11, 2007 by Soltz et al., the entire contents of which are hereby incorporated by reference.

BACKGROUND

1. Technical Field

The present disclosure relates to a multi-part surgical staple assembly. More particularly, the present disclosure relates to a multi-part surgical staple assembly having augmented compression areas to provide uniform compression across a staple line in tissue.

2. Background of Related Art

During surgical procedures involving operations on tubular tissue sections it is often necessary to cut or segment the tubular tissue sections and staple them closed. One instance of this type surgery involves cutting out a diseased section of a tubular tissue section such as, for example, a section of a colon and temporarily staple of the healthy, free ends of the tubular tissue section closed prior to reattaching them together. A line or row of staples is typically placed across the tubular tissue section. In some instances, fluid pressure remains within the tubular tissue sections and exerts stresses or forces on the staple lines placed across the tubular tissue sections.

Failure at the tissue line may occur resulting in the luminal contents leaking into the abdominal cavity potentially causing morbidity or mortality. Failures such as these have been attributed to the staple interaction with the underlying tissue. Leaks may form either through the staple penetration holes through the tissue or between the compressed layers of tissue themselves.

In addition, during the wound healing processes of the stapled tissues, the mechanical strength of the tissues may decrease over time. The decrease in mechanical strength corresponds to a decrease in compressive properties within the tissues resulting in the possibility of leakage. Further, there exists the relationship between the leak pressure of a anastomosis or staple line junction and the amount of clamping pressure applied by the staples. If the pressure within the lumen exceeds the compressive stresses, then a leak will form. This can be represented by the formula $P > \sigma t/r$ where $P$ is the pressure within the lumen, $\sigma$ is the compressive stress, $t$ is the thickness of the tissue and $r$ is the radius of the tubular tissue section.

Therefore, it would be desirable to provide a staple assembly capable of reducing leakage through tissue about staple legs of the staple assembly. It would further be desirable to provide a staple assembly capable of applying uniform compression across the areas of tissue secured by a staple of the staple assembly. It would still further be desirable to provide a staple assembly capable of compensating for losses in mechanical strength of the underlying tissue by maintaining constant compression levels on the stapled tissue.

SUMMARY

There is disclosed a surgical staple assembly for providing uniform compression to opposed sides of a stapled tissue section. The surgical staple assembly includes a U-shaped staple having a backspan and a pair of legs extending from the backspan, each of the legs terminating in a tissue penetrating tip. The surgical staple assembly also includes a first compression member having first openings for receipt of the legs of the staple and a second compression member having second openings for receipt of the legs of the staple. In use, the first compression member applies a first compressive force to a first side of a tissue section penetrated by the legs of the staple and the second compression member applies a second compressive force to a second side of the tissue section penetrated by the legs of the staple.

The first compression member is a generally flat plate having a length greater than a length of the back span of the staple and a width greater than a diameter of the material forming the staple. The second compression member is a platen having width greater than the diameter of the material forming the staple.

The platen further includes at least one third opening for accommodating the tissue penetrating tips of the staple. The at least one third opening is positioned adjacent the center of the platen. In one embodiment, the at least one third opening is an oval opening for receipt of the tissue penetrating tips of the staple.

In one embodiment of the surgical staple assembly, the plate includes a biasing member engagable with the backspan of the staple to bias the plate away from the backspan. In a specific embodiment, the biasing member is a leaf spring. The leaf spring may be formed integral with the plate or, alternatively, one end of the leaf spring may be affixed to the plate.

There is also disclosed a surgical staple assembly including a U-shaped staple having a backspan and a pair of legs extending from the backspan, each of the legs terminating in a tissue penetrating tip and a plate having openings for receipt of the legs of the staple. The plate includes a biasing member engagable with the backspan of the staple to bias the plate away from the backspan. The biasing member is a leaf spring and in one embodiment, the leaf spring is formed integral with the plate while in an alternative embodiment, one end of the leaf spring is affixed to the plate.

There is further disclosed a surgical staple assembly including a U-shaped staple having a backspan and a pair of legs extending from the backspan, each of the legs terminating in a tissue penetrating tip and a platen having first openings for receipt of the legs of the staple and at least one second opening for receipt of the tissue penetrating tips of the staple.

The at least one second opening is positioned between the first openings. Specifically, the at least one second opening is positioned in the center of the platen. In a particular embodiment, the at least one second opening is an oval opening for receipt of the tissue penetrating tips of the staple.

There is also disclosed an anvil for use with a surgical staple assembly incorporating a compression member. The anvil includes a plate having first staple clinching pocket and a second staple clinching pocket spaced apart from the first staple clinching pocket and at least one recess formed in the plate and extending from one of the first and second staple clinching pockets. The at least one recess is provided for receipt of an end of a compression member associated with a surgical staple assembly. In a specific embodiment, the at least one recess includes a first recess formed adjacent the first staple clinching pocket and a second recess formed adjacent the second staple clinching pocket.

In one embodiment of the anvil, the first staple clinching pocket includes a first center point, the first recess includes a first recess center point and the second staple clinching pocket includes a second center point. The first center point, first recess center point and the second center point lie along a common axis.

The plate further includes a central recess intermediate the first and second staple clinching pockets. The central recess has a raised portion, such that the raised portion is positioned beneath a central opening in the compression member.

DESCRIPTION OF THE DRAWINGS

Various embodiments of the presently disclosed augmented compression surgical staple are disclosed herein with reference to the drawings, wherein:

FIG. 5 is a perspective view of the staple assembly;

FIG. 6 is a side view of the platen;

FIG. 7 is a side view of the assembled and formed staple assembly;

FIG. 8 is a perspective view of an alternate embodiment of a staple assembly;

FIG. 9 is a side view of the staple assembly of FIG. 8 in the formed condition;

FIG. 10 is a perspective view of another embodiment of a staple assembly;

FIG. 11 is a side view of the staple assembly of FIG. 10 in the formed condition;

FIG. 15 is a perspective view of the staple assembly securing the tissue section and in the formed condition;

FIG. 16 is a side view, partially shown in section, of the staple assembly of FIG. 8 being driven through a tissue section; and FIG. 17 is a perspective view of the staple assembly of FIG. 16 securing the tissue section and in the formed condition.

DETAILED DESCRIPTION OF EMBODIMENTS

Embodiments of the presently disclosed surgical staple assembly and associated anvil for forming the surgical staple assembly will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
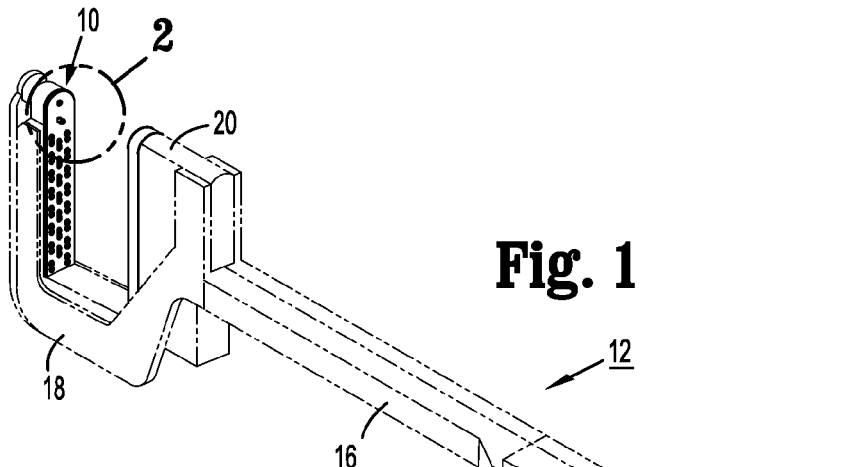
FIG. 1 is a perspective view of a surgical stapler incorporating one embodiment of an augmented compression surgical staple and associated anvil.

Referring initially to FIG. 1, there is disclosed an anvil 10 for use with a surgical stapler 12. Surgical stapler 12 is of the type typically used for open surgery procedures and includes a pistol grip handle 14 having an elongate member 16 extending distally from handle 14. Elongate member 16 terminates in a generally U-shaped anvil support 18. Anvil 10 is mounted on anvil support 18. Surgical stapler 12 also includes a staple containing head or staple head 20 which contains a plurality of staples as described in more detail hereinbelow. An adjustment knob 22 is provided on handle 14 and operates to move staple head 20 relative to anvil 10 in known manner in order to capture the tissue to be stapled therebetween. A trigger 24 is provided to actuate stapler 12 and eject staples out of staple head 20, through tissue and into anvil 10. A trigger lock 26 is provided to prevent movement of trigger 24 and thus premature actuation of surgical stapler 12. Although shown as an open-type surgical stapler, it is contemplated that the present disclosure can be readily used on any type of surgical stapler, ether open or endoscopic type staplers.

Figure 2:
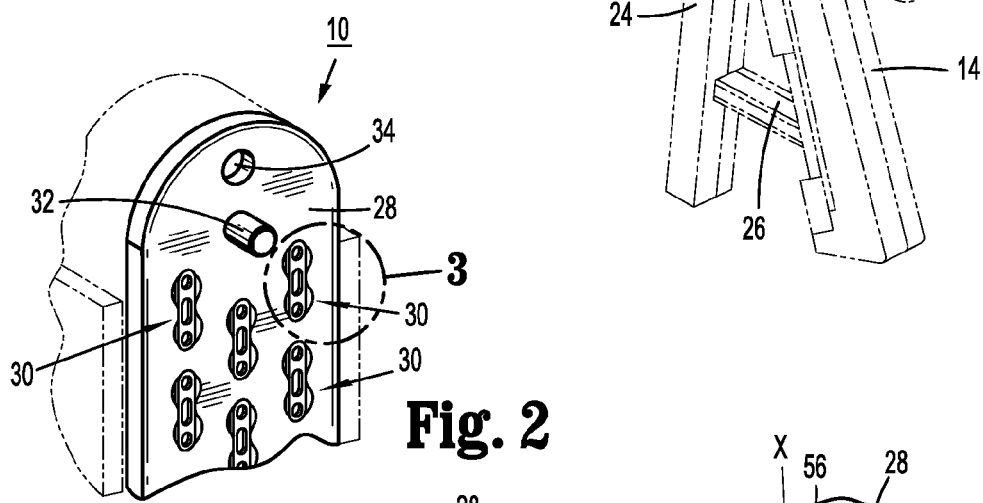
FIG. 2 is an enlarged area of detail of FIG. 1 illustrating anvil and staple assembly components.

Referring now to FIG. 2, anvil 10 includes an anvil plate 28 which is mounted to anvil support 18. Anvil plate 28 defines a plurality of staple forming pockets 30 which cooperate with staple head 20 to form, and support part of, a staple assembly. Anvil plate includes an alignment pin 32 and an alignment recess 34 which cooperate with a corresponding recess and pin on staple head 20 to ensure staples contained within staple head 20 are in proper alignment with staple forming pockets 30 during stapling of tissue.

Figure 3:
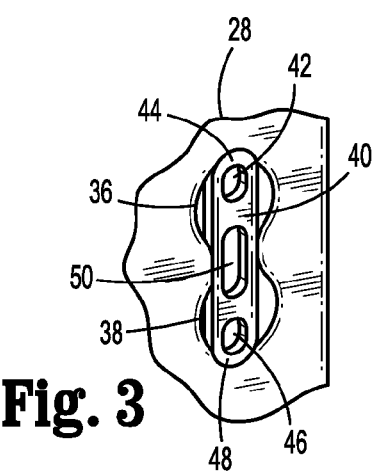
FIG. 3. is an enlarged area of detail view of FIG. 1 illustrating a staple clinching pocket of the anvil and a platen of the staple assembly.

With reference to FIG. 3, staple forming pocket 30 generally includes a first staple clinching depression or pocket 36 and a second staple clinching pocket 38 spaced apart from first staple clinching pocket 36. Pockets 36 and 38 are provided to receive tips of a staple and direct them toward a platen 40, associated with the surgical staple assembly, positioned within staple forming pocket 30. Platen 40 is formed as a generally elongated plate having a first hole 42 adjacent a first end 44 of platen 40 and a second hole 46 adjacent a second end 48 of platen 40. First and second holes 42 and 46 are provided to receive the legs of a surgical staple therethrough and direct them into first and second staple clinching pockets 36 and 38, respectively. Platen 40 further includes an opening 50 which is generally oval in shape and provided centrally along platen 40. Opening 50 is provided to receive tissue penetrating tips of the surgical staple associated with the surgical staple assembly in a manner described in more detail hereinbelow.

Figure 4:
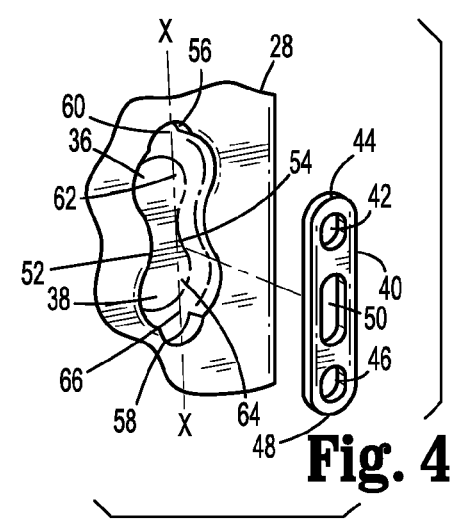
FIG. 4 is a perspective view, similar to FIG. 3, with the platen separated from the staple pocket.

As shown in FIG. 4, staple forming pocket 30 is provided with a narrowed central area or recess 52 located between first and second staple clinching pockets 36 and 38. A hump or protrusion 54 is located within recess 52 to assist in forming the staple of the surgical staple assembly. Recess 52 is located directly beneath opening 50 of platen 40 to direct the tips of the surgical staple associated with the surgical staple assembly through opening 50 of platen 40.

Platen 40 is frictionally retained within staple forming pocket 30. Staple pocket 30 includes a first retention recess 56 formed adjacent first staple clinching pocket 36 and a second retention recess 58 formed adjacent second staple clinching pocket 38. First and second ends 44 and 48 of platinum 40 are frictionally retained within first and second retention recesses 56 and 58 of staple forming pocket 30, respectively.

In a particular embodiment, first retention recess 56 includes a first retention center point 60, first staple clinching pocket 36 includes a first center point 62, second staple clinching pocket 38 includes a center point 64 and second retention recess 58 includes a second retention center point 66. As shown, in this particular embodiment, first retention center point 60, first center point 62 and second center point 64 lie along a common axis X-X. In a more specific embodiment, second retention center point 66 also lies along common axis X-X.

Referring now to FIG. 5, there is disclosed a novel, multipart staple assembly 68, including platen 40, capable of providing uniform compression along opposed sides of stapled tissue. Staple assembly 68 includes a generally U-shaped staple 70. Staple 70 is of a known type commonly used in the surgical arts and generally includes a backspan 72 and first and second legs 74 and 76 extending from first and second ends 78 and 80, respectively, of backspan 72. First and second legs 74 and 76 terminate in first and second tissue penetrating tips 82 and 84, respectively.

In order to provide uniform compression along both sides of tissue to be stapled, staple assembly 68 further includes a staple plate 86. Staple plate 86 is provided with a first plate hole 88 at a first end 90 thereof and a second plate hole 92 formed in a second end 94 of staple plate 86. First and second plate holes 88 and 92 are provided to receive staple legs 74 and 76 therethrough. It should be noted that the overall lengths of platen 40 and staple plate 86 are inherently longer than the backspan 72 of staple 70 and the widths of platen 40 and staple plate 86 are inherently wider than the diameter of the material forming surgical staple 70. It should be further noted that the provision of platen 40 and staple plate 86 augment the compression area which would otherwise be provided on stapled tissue by surgical staple 70 alone.

Referring for the moment to FIG. 6, platen 40 is illustrated in cross-section. As shown, central opening 50 is located intermediate first and second holes 42 and 46 in platen 40. In the embodiment specifically illustrated, central opening 50 is located centrally along the length of platen 40 so as to receive any excess length of tissue penetrating tips 82 and 84 as they are formed within staple forming pocket 30 of anvil 10.

Referring now to FIG. 7, upon being formed within a surgical stapling apparatus, surgical staple 70 is formed into a typical B-shape. As shown, leg 74 of surgical staple 70 passes through first plate hole 88 in staple plate 86 and through first hole 42 in platen 40. Similarly, second leg 76 passes through second plate hole 92 in staple plate 86 and through second hole 46 in platen 40. Upon being formed within staple forming pocket 30 of anvil 10, tissue penetrating tips 74 and 76 are recurved back towards backspan 72 of staple 70 and may pass through central opening 50 depending on the particular thickness of the tissue being stapled. This allows surgical staple assembly 68 to accommodate various thicknesses of tissue. For example, when used with particularly thin tissue sections, the passage of tissue penetrating tips 74 and 76 through central opening 50 take-up any excess length in staple legs 74 and 76 and allow complete compression of the stapled tissue sections.

Turning now to FIG. 8, there is disclosed in alternative embodiment of a surgical staple assembly 96 incorporating platen 40 and surgical staple 72 substantially as described hereinabove. Surgical staple assembly 96 includes an alternate embodiment of a staple plate 98 having a biasing member 100 which is provided to urge staple plate 98 away from backspan 72 of surgical staple 70. The provision of biasing member 100 on staple plate 98 allows staple plate 98 to provide a consistent degree of pressure against underlying stapled tissues. This is particularly useful when, as noted above, the stapled tissue loses mechanical strength due to compression, degradation, necrosis, etc. over time. This ensures that, as the stapled tissue weakens over time, surgical staple assembly 96 provide sufficient compression to prevent any leakage through the underlying stapled tissue sections until such time as the underlying tissue sections have properly healed.

In this particular embodiment, biasing member 100 is integrally formed with staple plate 98. Staple plate 98 may be formed of any suitable material capable of providing a certain amount of flexion within biasing member 100. Biasing member 100 may be formed in staple plate 98 by stamping, molding, etc. Biasing member 100 includes a first end 102 extending from a first point 104 on staple plate 98 and extending to a second end 106 at a second point 108 on staple plate 98. When biasing member 100 is stamped, punched or otherwise cut from staple plate 98, the material occupied by biasing member 100 results and an opening 110 formed in staple plate 98. It should be noted that, while biasing member 100 is disclosed as being connected at first and second ends 102 and 106 to staple plate 98, one of first end 102 or second and 106 may be cut or otherwise disconnected from staple plate 98 20 allow a greater degree of flexion, and thus of biasing force, of biasing member 100. In this instance, biasing member 100 generally functions as a leaf spring.

Staple plate 98 additionally includes a first hole 112 formed at a first end 114 of staple plate 98 and a second hole 116 formed at a second end 118 of staple plate 98. First and second holes 112 and 116 are provided to receive staple legs 74 and 76 therethrough in a manner similar to that described hereinabove with respect to staple plate 86.

As best shown in FIG. 9, when surgical staple assembly 96 is fully formed, first and second legs 74 and 76 extend through first and second holes 112 and 116, respectively, in staple plate 98. As described hereinabove with regard to surgical staple assembly 68, fully formed staple 70 assumes a general B-shape with tissue penetrating tips 82 and 84 extending through first and second holes 42 and 46 in platen 40.

As noted hereinabove, platen 40 is initially retained within anvil 10. Common to all the staple assembly embodiments disclosed herein, as surgical staple 70 is formed into a general B-shape within staple forming pocket 30 of anvil 10, tissue penetrating tips 82 and 84 engage first and second edges 120 and 122, respectively, of central opening 50 in platen 40. The engagement of tissue penetrating tips 82 and 84 with edges 120 and 122 function to force or "pop" platen 40 free from its friction fit within staple forming pocket 30.

Referring now to FIGS. 10 and 11, there is disclosed a further embodiment of a surgical staple assembly 124 including platen 40 and surgical staple 70 substantially as described hereinabove. Surgical staple assembly 124 includes a staple plate 126 having a biasing member 128 affixed to staple plate 126. Biasing member 128 may be affixed to staple plate 126 by welding, gluing, etc. As with biasing member 100 hereinabove, biasing member 128 may be affixed to staple plate 126 at only one end and function as a leaf spring. Additionally, biasing member 128 may be formed of a material different from that of staple plate 126. Similar to those staple plates described hereinabove, staple plate 126 includes a first hole 130 formed in a first end 132 of staple plate 126 and a second hole 134 formed in a second end 136 thereof. As with staple plate 98 described hereinabove, biasing member 128 is provided to urge staple plate 126 away from backspan 72 and toward surgical staple 70 to provide a consistent pressure of staple plate 126 against underlying stapled tissue.

Figure 12:
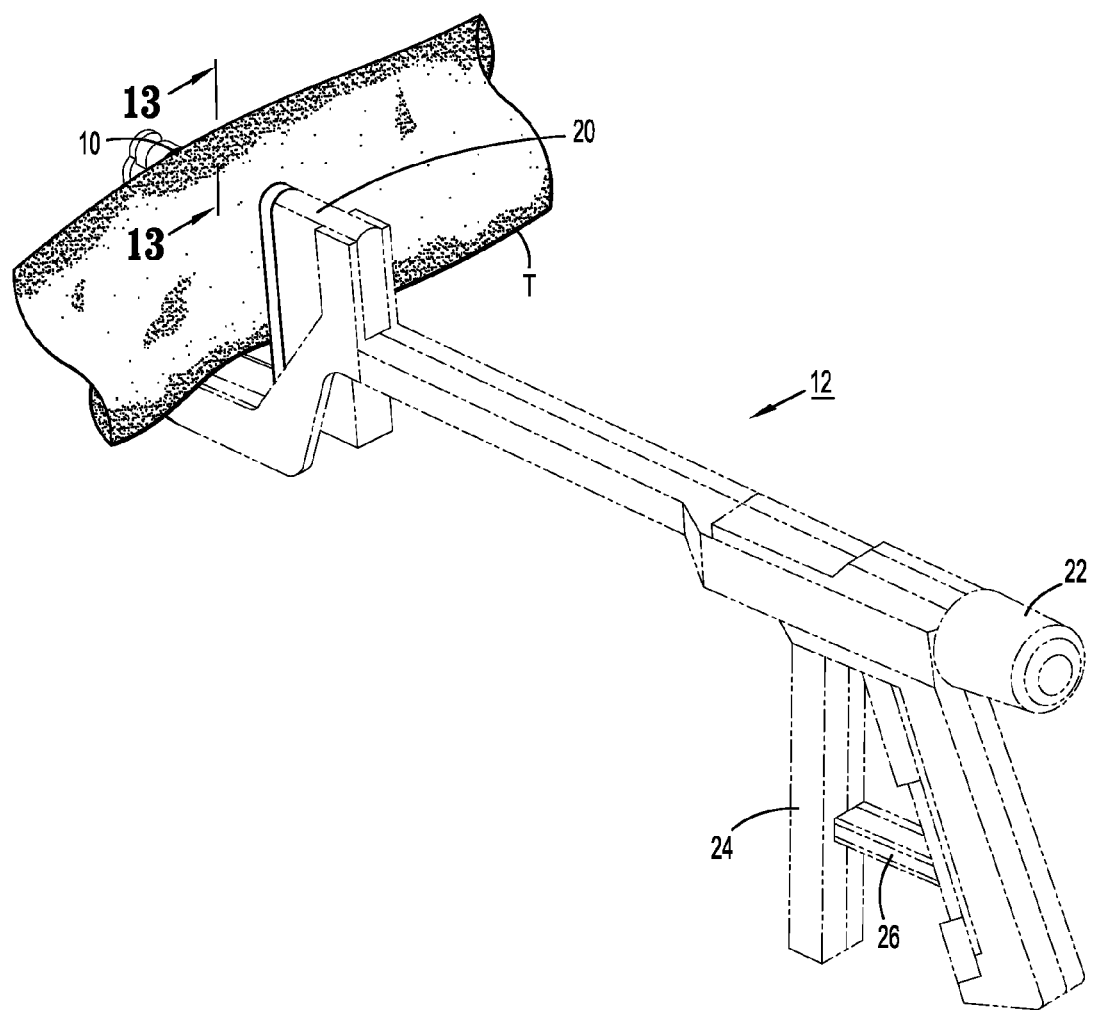
FIG. 12 is a perspective view of the surgical instrument of FIG. 1 positioned about a tissue section.

Referring now to FIGS. 12-15, and initially with regard to FIG. 12, the use of staple assembly 68 and anvil 10, incorporated into surgical stapler 12, to staple a tubular tissue T will now be described. It should be noted that, while the following discussion of the use of staple assembly 68 and anvil 10 is given in connection with an open surgery style surgical stapler 12, staple assembly 68 and anvil 10 find equal application when used in other types of surgical staplers, such as, for example, endoscopic or laparoscopic staplers, circular or anastomotic staplers, etc. Further, staple assembly 68 and anvil 10 are equally suited for use in stapling tissues other than tubular tissue sections and need not necessarily be used in conjunction with one another.

Surgical stapler 12 is provided with a plurality of staples 70 and staple plates 86 loaded in staple head 20 in a manner discussed in more detail hereinbelow. Surgical stapler 12 is initially placed such that tissue section T is positioned between anvil 10 and staple head 20. Thereafter, adjustment knob 22 is manipulated to move staple head 20 toward anvil 10 and capture tissue T therebetween.

Figure 13:
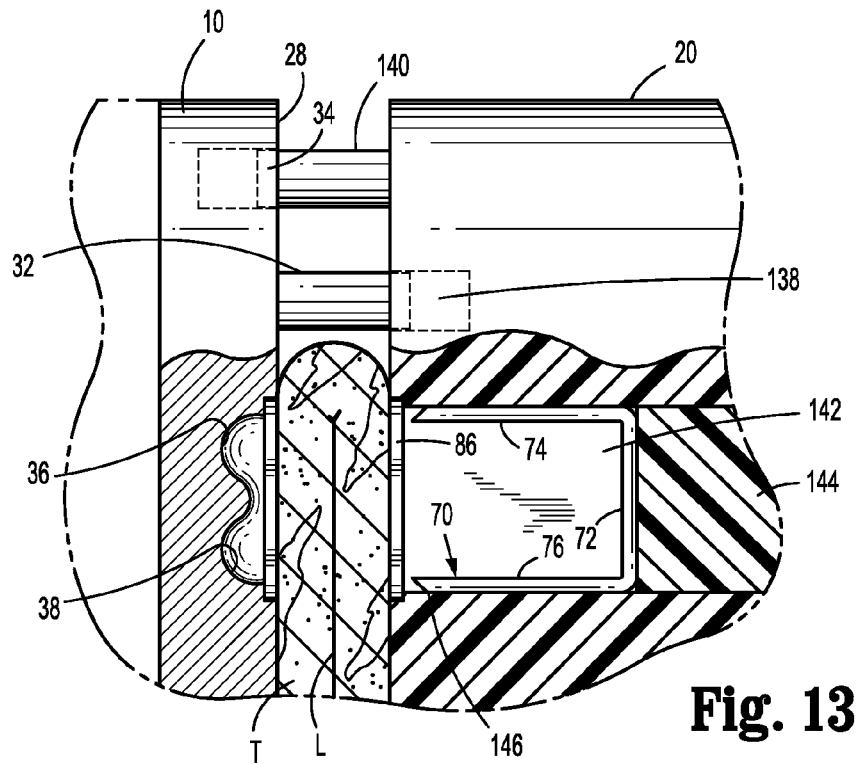
FIG. 13 is a side view, partially shown in section, of the tissue section captured between the anvil and a staple head of the surgical stapler.

As shown in FIG. 13, captured tubular tissue T is captured and compressed between anvil 10 and staple head 20 to close lumen L in tubular tissue T. Upon movement of staple head 20 toward anvil 10, alignment pin 32 on anvil plate 28 enters a recess 138 in staple head 20 and a staple head pin 140 on staple head 20 enters alignment recess 34 in anvil plate 28 to ensure proper alignment of staple legs 74 and 76 with staple clinching pockets 36 and 38, respectively. As noted above, staple head 20 is provided with a plurality of staples 70 and staple plates 86. Specifically, staples 70 are contained within staple pockets, such as staple pocket 142, formed in staple head 20. A pusher 144 is positioned within staple pocket 142 and is movable within staple pocket 142 in response to actuation of trigger 24 of surgical stapler 12. Movement of pusher 144 within staple pocket 142 causes pusher 144 to engage backspan 72 of staple 70 and drive staple 70 out of staple head 20 toward anvil 10.

Staple plate 86 is frictionally retained within a staple plate recess 146 formed in staple head 20 and positioned over staple pocket 142 in order to positioned staple plate 86 in front of staple 70.

Figure 14:
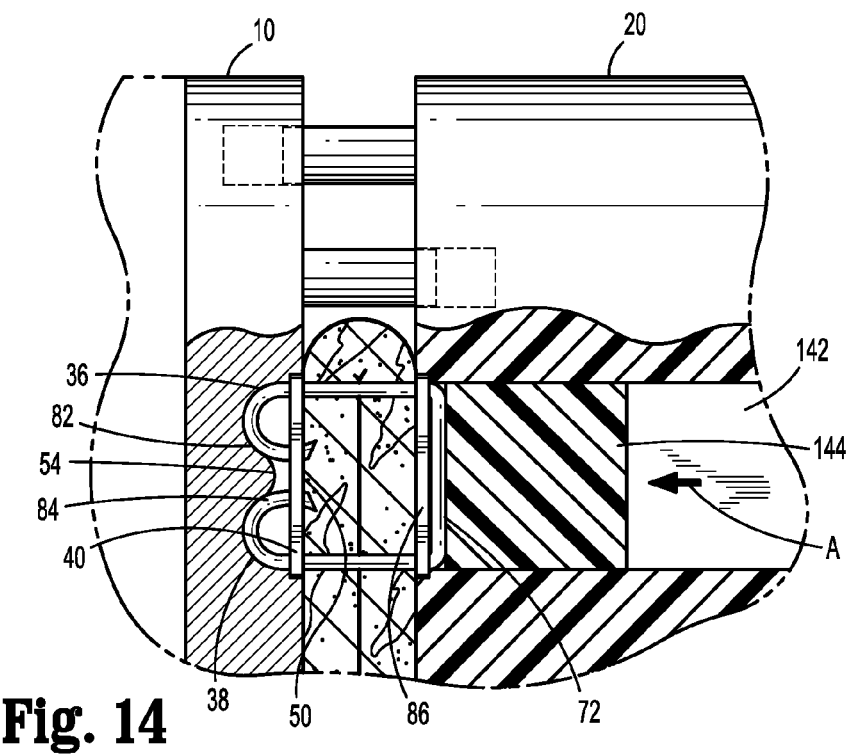
FIG. 14 is a side view, partially shown in section, illustrating a staple of the staple assembly being driven through the tissue section.

Referring now to FIGS. 12 and 14, once surgical stapler 12 has been positioned about tissue T, lock lever 26 is disengaged from trigger 24 and trigger 24 is actuated (FIG. 12) to cause driver 144 to move distally within staple pocket 142 (FIG. 14), as indicated by arrow A in FIG. 14. With continued reference to FIG. 14, pusher 144 drives staple 70 distally within staple pocket 142 such that tissue penetrating tips 82, 84 pass through holes 88 and 92 in staple plate 86 as described hereinabove (FIG. 7) and thereafter through tissue T. After penetrating tissue T, tissue penetrating tips 82 and 84 pass through holes 42 and 46 in platen 40 (FIG. 7) and are formed within staple clinching pockets 36 and 38 in anvil plate 28. As noted hereinabove, engagement of tips 82 and 84 with protrusion 54 cause tips 82 and 84 to recurve back toward backspan 72 of staple 70 and pass through central opening 50 formed in platen 40.

Upon full actuation of surgical stapler 12, pusher 144 urges staple 70 out of staple pocket 142 which in turn pushes staple plate 86 free of its frictional engagement within staple plate recess 146 in staple head 20 thereby releasing staple 70 and staple plate 86 from staple head 20. As discussed hereinabove, engagement of tissue penetrating tips 82 and 84 with edges of central opening 50 in platen 44 force or "pop" platen 40 free of its frictional engagement in staple forming pocket 30.

Surgical staple assembly 68, fully formed and closing lumen L of tissue T, is best illustrated in FIG. 15. The provisions of platen 40 and staple plate 86 in surgical staple assembly 68 provide a greater, and more uniform, compression area to tissue T over that as would otherwise be provided by staple 70 alone.

Referring for the moment to FIGS. 16 and 17, surgical staple assembly 96 is assembled within surgical stapler 12 and driven through tubular tissue section T in a manner substantially identical to that described hereinabove with respect to surgical staple assembly 68. For example, pusher 144 moves distally within staple pocket 142, as indicated by arrow B in FIG. 16, to drive staple 72 out of staple pocket 142, through staple plate 98 and tissue T. Thereafter, tissue penetrating tips 82 and 84 pass through platen 40 to fully form surgical staple assembly 96 about tissue T. As noted hereinabove, surgical staple assembly 96 includes biasing member 100 to provide a constant pressure of staple plate 98 against tissue T over time. This ensures a constant level of pressure force against stapled tissue T by staple plate 86 and platen 40 thereby preventing any leakage through lumen L in the event that the structural strength of tissue T degrades and the thickness of tissue T decreases over time.

While not specifically shown, it should be noted that surgical staple assembly 124, including biasing member 128, functions substantially identically to surgical staple assembly 96.

It will be understood that various modifications may be made to the embodiments disclosed herein. For example, the disclosed platens may take other shapes and sizes and do not necessarily need to be longer than the overall length of the backspan of the staple used therewith. Further, the disclosed platens may be formed without a central opening to provide a greater surface area for compression against a stapled tissue section. Additionally, biasing members may also be provided on the platen to urge the platen away from the legs or tissue penetrating tips of the staples and towards the tissue section to provide a constant source of pressure against the stapled tissue section overtime. Therefore, the above description should not be construed as limiting, but merely as exemplifications of particular embodiments. Those skilled in the art will envision other modifications within the scope and spirit of the claims appended hereto.

What is claimed is:

1. An anvil and a compression member assembly comprising:
    a compression member including first and second ends and first and second edges; and
    an anvil including,
        a plate having a first staple clinching pocket and a second staple clinching pocket positioned adjacent to the first staple clinching pocket; and
        first and second recesses formed in the plate, each of the first and second recesses extending outwardly from a respective one of the first and second staple clinching pockets, the first and second recesses being configured to receive a respective one of the first and second ends of the compression member, wherein the compression member is received entirely within the first and second staple clinching pockets and the first and second recesses of the plate and the first and second edges of the compression member are positioned to be engaged by penetrating tips of a staple to force the compression member from within the first and second staple clinching pockets and the first and second recesses.

2. The anvil and the compression member assembly as recited in claim 1, wherein the first recess is formed adjacent the first staple clinching pocket and the second recess is formed adjacent the second staple clinching pocket.

3. The anvil and the compression member assembly as recited in claim 2, wherein the first staple clinching pocket includes a first center point, the first recess includes a first recess center point, and the second staple clinching pocket includes a second center point such that the first center point, first recess center point and the second center point lie along a common axis.

4. The anvil and the compression member assembly as recited in claim 1, wherein the plate further includes a central recess intermediate the first and second staple clinching pockets, the central recess having a raised portion, such that the raised portion is positioned beneath a central opening in the compression member.

5. The anvil and the compression member assembly as recited in claim 1, wherein the first recess is formed outward of the first staple clinching pocket and the second recess is formed outward of the second staple clinching pocket.

6. The anvil and the compression member assembly as recited in claim 5, wherein the first end of the compression member is received in the first recess and the second end of the compression member is received in the second recess.

7. The anvil and the compression member assembly as recited in claim 1, wherein the first and second staple clinching pockets each include a staple forming surface extending a length of each of the first and second staple clinching pockets.

8. The anvil and the compression member assembly as recited in claim 1, wherein the compression member and the plate each includes a tissue contacting surface, the tissue contacting surface of the compression member laying flush with the tissue contacting surface of the plate when the compression member is received within the plate.

9. An anvil and a compression member assembly comprising:
   a compression member including first and second edges; and
   an anvil including a plate having a first staple clinching pocket and a second staple clinching pocket positioned adjacent to the first staple clinching pocket, the compression member being frictionally received within the first and second staple clinching pockets, wherein the first and second edges of the compression member are positioned to be engaged by penetrating tips of a staple to force the compression member free from within the first and second staple clinching pockets; wherein the anvil further includes first and second recesses formed in the plate and the compression member includes first and second ends, wherein each of the first and second recesses extend outwardly from a respective one of the first and second staple clinching pockets and are configured to receive a respective one of the first and second ends of the compression member.

\* \* \* \* \*